US009242016B2

(12) United States Patent
Robertson et al.

(10) Patent No.: US 9,242,016 B2
(45) Date of Patent: Jan. 26, 2016

(54) GOLD COATED LANTHANIDE NANOPARTICLES

(75) Inventors: John David Robertson, Columbia, MO (US); Mark F. McLaughlin, Columbia, MO (US); Paul H. Pevsner, New York, NY (US)

(73) Assignee: The Curators of the University of Missouri, Columbia, MO (US)

( * ) Notice: Subject to any disclaimer, the term of this patent is extended or adjusted under 35 U.S.C. 154(b) by 948 days.

(21) Appl. No.: 13/342,823

(22) Filed: Jan. 3, 2012

(65) Prior Publication Data

US 2013/0004417 A1 Jan. 3, 2013

Related U.S. Application Data

(60) Provisional application No. 61/460,528, filed on Jan. 3, 2011.

(51) Int. Cl.

| | |
|---|---|
| ***A61K 51/00*** | (2006.01) |
| ***A61M 36/14*** | (2006.01) |
| ***A61K 51/12*** | (2006.01) |
| ***B82Y 40/00*** | (2011.01) |
| ***B82Y 30/00*** | (2011.01) |

(52) U.S. Cl.

CPC ............. *A61K 51/1244* (2013.01); *B82Y 30/00* (2013.01); *B82Y 40/00* (2013.01)

(58) Field of Classification Search

CPC ..... A61K 51/00; A61K 51/02; A61K 51/025; A61K 51/0489; A61K 51/06; A61K 51/065; A61K 51/12; A61K 51/1241; A61K 51/1244; A61K 51/1251; A61K 2121/00; A61K 2123/00; B82Y 30/00; B82Y 40/00

USPC .......... 424/1.11, 1.65, 1.77, 9.1, 9.2, 9.3, 9.4, 424/9.5, 9.6, 400, 489, 490, 1.29; 977/700, 977/773

See application file for complete search history.

(56) References Cited

U.S. PATENT DOCUMENTS 7,629,291 B2 12/2009 Dai et al.

OTHER PUBLICATIONS

Buissette et al., "Aqueous Routes to Lanthanide-Doped Oxide Nanophosphors", Journal of Materials Chemistry, 2006, pp. 529-539, vol. 16.

Buissette et al., "Collodial Synthesis of Luminescent Rhabdophane LaPO4:LN3+•xH2O (Ln = Ce, Tb, Eu; x 0.7) Nanocrystals", Chemistry of Materials, 2004, pp. 3767-3773, vol. 16, No. 19.

Buissette et al., "Luminescent Core/Shell Nanoparticles with a Rhabdophane LnPO4-xH2O Structure: Stabilization of Ce3+-Doped Compositions", Advanced Functional Materials, 2006, pp. 351-355, vol. 16.

Dixit et al., "Synthesis and Grafting of Thioctic Acid-PEG-Folate Conjugates onto Au Nanoparticles for Selective Targeting of Folate Receptor-Positive Tumor Cells", Bioconjugate Chemistry, 2006, pp. 603-609, vol. 17, No. 3.

Hifumi et al., "Dextran Coated Gadolinium Phosphate Nanoparticles for Magnetic Resonance Tumor Imaging", Journal of Materials Chemistry, 2009, pp. 6393-6399, vol. 19.

Jaggi et al., "Efforts to Control the Errant Products of a Targeted In vivo Generator", Cancer Research, Jun. 1, 2005, pp. 4888-4895, vol. 65 No. 11.

Kimling et al., "Turkevich Method for Gold Nanoparticle Synthesis Revisited", Journal of Physical Chemistry, 2006, pp. 15700-15707, vol. 110, No. 32.

McDevitt et al., "Radioimmunotherapy with Alpha-Emitting Nuclides", European Journal of Nuclear Medicine, Sep. 1998, pp. 1341-1351, vol. 25, No. 9.

McDevitt et al., "Tumor Therapy with Targeted Atomic Nanogenerators", Science, Nov. 16, 2001, pp. 1537-1540, vol. 294.

Meiser et al., "Biofunctionalization of Fluorescent Rare-Earth-Doped Lanthanum Phosphate Colloidal Nanoparticles", Angewandte Chemie International Edition, 2004, pp. 5954-5957, vol. 43.

Miederer et al., "Pharmacokinetics, Dosimetry, and Toxicity of the Targetable Atomic Generator, 225Ac-HuM195, in Nonhuman Primates", Journal of Nuclear Medicine, Jan. 2004, pp. 129-137, vol. 45, No. 1.

O'Donoghue, "Relevance of External Beam Dose-Response Relationships to Kidney Toxicity Associated with Radionuclide Therapy", Cancer Biotherapy & Radiopharmaceuticals, 2004, pp. 378-387, vol. 19, No. 3.

Van Vlerken et al., "Poly(ethylene glycol)-Modified Nanocarriers for Tumor-Targeted and Intracellular Delivery", Pharmaceutical Research, 2007, 10 pages.

Woodward et al., "LaPO4 Nanoparticles Doped with Actinium-225 that Partially Sequester Daughter Radionuclides", Bioconjugate Chemistry, 2011, pp. 766-776, vol. 22.

*Primary Examiner* — D L Jones

(74) *Attorney, Agent, or Firm* — Thompson Coburn LLP

(57) ABSTRACT

The present invention is directed α-particle emitting nanoparticles that comprise a lanthanide phosphate sequestration shell enclosing an α-emitting-radioisotope-doped lanthanide phosphate core such that the shell allows at least some of the α emissions from the α-emitting radioisotope to pass therethrough and prevents at least some radioactive decay products of the α-emitting radioisotope from exiting the α-particle emitting nanoparticle. Further, such α-particle emitting nanoparticles may be coated with gold and functionalized. Additionally, a method for making and using the same are disclosed.

53 Claims, No Drawings

GOLD COATED LANTHANIDE NANOPARTICLES

CROSS-REFERENCE TO RELATED APPLICATIONS

The present application is a non-provisional application claiming the benefit of 61/460,528, filed Jan. 3, 2011, which is incorporated herein by reference in its entirety.

BACKGROUND OF INVENTION

Therapeutics based on α radiation provide a promising alternative to conventional methodologies (e.g., γ radiation and $\beta^-$ radiation) because α radiation relatively short particle range results in substantially lesser radiation to neighboring tissue. Specifically, instead of being used to treat large, solid tumors, α particles have a greater potential for application to small, disseminated tumors, and micro metastases. Development of effective α therapeutics would also provide a boon to treatment of hematological malignancies consisting of individual, circulating neoplasmic cells. Compared with $\beta^-$ radiation, α radiation provides a very high relative biological effectiveness, killing more cells with a lower activity. This effect results from the high linear energy transfer of α particles, inducing more DNA double strand breaks per decay than their $\beta^-$ counterparts. Additionally, due to the direct action of α radiation on DNA without free radical intermediaries, it remains unaffected by hypoxic environments and cell cycle considerations. Further, a relatively low γ component in the decay of alpha emitters tends to allow for outpatient treatments while also making it easier to protect nuclear medicine personnel.

Nevertheless, α emitters pose distinct chemical problems for their development and therapeutic use. Several radionuclide options emit multiple α particles in their decay chain. These therapeutic in vivo generator systems can deliver a relatively large amount of energy in a localized space (e.g., $^{225}$Ac and daughters deliver >27 MeV of energy). Unfortunately, if long-lived daughter products are not retained within the structure of the therapeutic, they are likely to migrate to non-target tissue. Generally, the first α emission provides enough recoil energy on the parent nucleus to sever any metal-ligand bond thereby releasing the daughter radionuclide from the targeting agent. Nanoparticles represent a desirable solution for an in vivo α radiation generator in that they represent a good size balance—small enough to have a targeting ability similar to that of small molecules but large enough to contain at least some radioactive decay daughters. In addition to sequestering at least some of the radioactive decay daughters due to their size, nanoparticles are believed to reduce kidney toxicity because they tend to be cleared preferentially through the liver, spleen, and other areas of the reticuloendothelial system rather than the renal system.

Of particular interest for therapeutic in vivo α radiation generator nanoparticles are $LaPO_4$ nanoparticles doped with $^{225}$Ac (see, e.g., Imaging of vascular targeted $LaPO_4$ nanoparticles doped with actinium-225, Kennel et al., Poster Session 2d: Development/Novel Use of Imaging Probes, Sep. 25, 2009) but such nanoparticles have several shortcomings. For example, such $^{225}$Ac-doped $LaPO_4$ nanoparticles tend to only sequester about 50% of the radioactive decay daughters (e.g., $^{221}$Fr). Additionally, the surfaces of such $^{225}$Ac-doped $LaPO_4$ nanoparticles are not readily functionalized such that the nanoparticles are generally considered to substantially target particular tissue types or locations in a body being treated therewith. Thus, a need still exists for nanoparticles doped with α emitting radionuclides having one or more of the following properties: improved retention or sequestration of radioactive decay products and surfaces that are readily functionalized so that the nanoparticles upon administration to a patient tend to target a desired tissue type(s) or location(s) in the body.

SUMMARY OF INVENTION

The present invention is directed to an α-particle emitting nanoparticle. The α-particle emitting nanoparticle comprises:

(a) an α-particle emitting core that comprises an α-emitting-radioisotope-doped $LnPO_4$; and (b) a sequestration shell enclosing the core that comprises $LnPO_4$ and is free of an α-emitting-radioisotope and that allows at least some of the α emissions from the α-emitting radioisotope to pass therethrough and prevents at least some radioactive decay products of the α-emitting radioisotope from exiting the α-particle emitting nanoparticle; and wherein Ln of the α-particle emitting core and the sequestration shell are separately selectable lanthanide elements from the group consisting of La, Gd, Sm, Eu, Tb, Dy, Ho, Lu, Nd, and combinations thereof, and the α-particle emitting radioisotope is selected from the group consisting of $^{225}$Ac, $^{223}$Ra, any radioactive decay products thereof, and combinations thereof.

The present invention is also directed to a method of making α-particle emitting nanoparticles each of which comprising an α-particle emitting core, which comprises an α-emitting-radioisotope-doped $LnPO_4$, and sequestration shell enclosing the core that allows at least some of the α emissions from the α-emitting radioisotope to pass therethrough and prevent at least some radioactive decay products of the α-emitting radioisotope from exiting the α-particle emitting nanoparticles, wherein the sequestration shell comprises one or more layers each which comprising $LnPO_4$ and is free of an α-emitting-radioisotope. The method comprising:

(a) treating a colloidal suspension that comprises particles, which comprise the α-particle emitting cores and any previously deposited layers, if any, dispersed in a shell solution, which comprises $Ln^{3+}$ cations and $PO_4^-$ containing anions, to cause the reaction of $Ln^{3+}$ cations and $(PO_4)^{3-}$ anions thereby resulting in the formation of one such layer on the particles; and (b) repeating step (a) until the desired number of layers is deposited; and wherein Ln of the α-particle emitting core and each layer of the sequestration shell are separately selectable lanthanide elements from the group consisting of La, Gd, Sm, Eu, Tb, Dy, Ho, Lu, Nd, and combinations thereof.

Additionally, the present invention is directed to a method of depositing coatings comprising gold on nanoparticles having $LnPO_4$ surfaces. The method comprising treating a mixture comprising the particles, solute gold ions, and solute citrate ions and reducing the solute gold ions such that at least some of the gold comes out of solution and deposits on the surfaces of the nanoparticles thereby forming the shells, wherein the mixture is formed by mixing a particle solution comprising the nanoparticles and the citrate ions and a gold-containing solution, and wherein the gold is at an amount that is in the range of about 0.1 mM to about 10 mM in the gold-containing solution, the citrate is at an amount that is in the range of about 0.001 M to about 0.1 M of the particle solution, the nanoparticles are at an amount that is in the range of about 0.1 mg/mL to about 10 mg/mL of the mixture, and the mass ratio of solute gold to nanoparticles to citrate in the mixture is about 0.6-60:0.1-10:1.2-120, and wherein the treating comprises controlling the temperature of the mixture such that it is in the range of about 50 to about 100° C. for a duration that is in the range of about 0.3 to about 3 hours.

Further, the present invention is directed to a composition for targeted in vivo generated alpha radiotherapy. The composition comprises:

(a) phosphate buffered saline; and (b) a multiplicity of α-particle emitting nanoparticles, wherein each such α-particle emitting nanoparticle comprises:

(i) an α-particle emitting core that comprises an α-emitting-radioisotope-doped $LnPO_4$; and (ii) a sequestration shell enclosing the core that comprises $LnPO_4$ and that is essentially free of the α-emitting-radioisotope, wherein the sequestration shell allows at least some of the α emissions from the α-emitting radioisotope to pass therethrough and prevents at least some radioactive decay products of the α-emitting radioisotope from exiting the α-particle emitting nanoparticle;

(iii) an outer coating covering the sequestration shell that comprises gold; and (iv) a surface functionalization component adhered to the outer coating, wherein the surface functionalization component comprises a linker component and target component; and wherein Ln of the α-particle emitting core and the sequestration shell are separately selectable lanthanide elements from the group consisting of La, Gd, Sm, Eu, Tb, Dy, Ho, Lu, Nd, and combinations thereof, and the α-particle emitting radioisotope is selected from the group consisting of $^{225}Ac$, $^{223}Ra$, any radioactive decay products thereof, and combinations thereof.

Still further, the present invention is directed to a method for conducting targeted in vivo generated alpha radiotherapy. The method comprising administering to a patient an effective amount of a composition comprising:

(a) phosphate buffered saline; and (b) a multiplicity of α-particle emitting nanoparticles, wherein each such α-particle emitting nanoparticle comprises:

(i) an α-particle emitting core that comprises an α-emitting-radioisotope-doped $LnPO_4$; and (ii) a sequestration shell enclosing the core that comprises $LnPO_4$ and that is essentially free of the α-emitting-radioisotope, wherein the sequestration shell allows at least some of the α emissions from the α-emitting radioisotope to pass therethrough and prevents at least some radioactive decay products of the α-emitting radioisotope from exiting the α-particle emitting nanoparticle;

(iii) an outer coating deposited on the sequestration shell that comprises gold; and (iv) a surface functionalization component adhered to the outer coating, wherein the surface functionalization component comprises a linker component and target component; and wherein Ln of the α-particle emitting core and the sequestration shell are separately selectable lanthanide elements from the group consisting of La, Gd, Sm, Eu, Tb, Dy, Ho, Lu, Nd, and combinations thereof, and the α-particle emitting radioisotope is selected from the group consisting of $^{225}Ac$, $^{223}Ra$, any radioactive decay products thereof, and combinations thereof.

Additionally, the present invention is directed to a β-particle emitting nanoparticle comprising a β-particle emitting core that comprises a β-emitting-radioisotope-doped $LnPO_4$, an outer coating deposited on the core that comprises gold, and a surface functionalization component adhered to the outer coating, wherein Ln are lanthanide elements from the group consisting of La, Gd, Sm, Eu, Tb, Dy, Ho, Lu, Nd, and combinations thereof, and wherein some portion of the Ln is a β-particle emitting radioisotope that is selected from the group consisting of $^{147}Nd$, $^{149}Pm$, $^{151}Pm$, $^{153}Sm$, $^{161}Tb$, $^{166}Ho$, $^{177}Lu$, and combinations.

DETAILED DESCRIPTION OF INVENTION

The present invention is directed, at least in part, to an α-particle emitting nanoparticle that comprises (a) an α-particle emitting core that comprises an α-emitting-radioisotope-doped lanthanide phosphate and (b) a sequestration shell enclosing the core that comprises a lanthanide phosphate and allows at least some of the α emissions from the α-emitting radioisotope to pass therethrough and prevents at least some radioactive decay products of the α-emitting radioisotope from exiting the α-particle emitting nanoparticle. To be clear, the use of the terms "radioactive decay product", "decay product", "daughter", "daughter product", "daughter nuclide", "daughter radionuclide", etc. are intended to be synonymous and are meant to refer to the remaining nuclide(s) left over from radioactive decay. In an embodiment of the present invention, the α-particle emitting nanoparticle consists of the α-particle emitting core and the sequestration shell. Advantageously, the present invention significantly improves the likelihood of developing safe and effective therapeutic treatments that harness the potential of multiple α-emitting decay chains, such as from $^{225}Ac$. For example, experimental results to date indicate that the inclusion of the aforementioned sequestration shell may be used to increase the retention of $^{221}Fr$ to as much as about 90% or even more.

α-Particle Emitting Core

As indicated above, the nanoparticles of the present invention comprise an α-particle emitting core that comprises an α-emitting-radioisotope-doped $LnPO_4$, wherein Ln represents lanthanide elements selected from the group consisting of La, Gd, Sm, Eu, Tb, Dy, Ho, Lu, Nd, and combinations thereof, and wherein the α-particle emitting radioisotope is selected from the group consisting of $^{225}Ac$, $^{223}Ra$, any radioactive decay products thereof, and combinations thereof. In an embodiment, the core consists of the α-emitting-radioisotope-doped $LnPO_4$. It is important to note that all references to lanthanide phosphates for both the core and the sequestration shell herein are intended to include hydrated forms.

In an embodiment, the α-particle emitting core has a diameter that is in the range of about 1 nm to about 10 nm. In an embodiment, the α-particle emitting core has a diameter that is in the range of about 2 nm to about 6 nm. In an embodiment, the α-particle emitting core has a diameter that is about 4 nm.

α-Emitting-Radioisotope-Doped $LnPO_4$

Experimental results to date indicate one may affect various characteristics of the nanoparticles based on the selection of the particular lanthanide elements and their respective amounts in the core and the sequestration shell. For example, experimental results to date suggest it may be desirable to select lanthanides for inclusion in the core that are of a size that is as close as possible to that of the parent radionuclide(s) in order improved the retention thereof. This is likely at least contributing factor underlying the observation that, for certain lanthanide phosphates in the $\{La_{0.0 \le x \le 1.0} Gd_{0.0 \le x \le 1.0}\}PO_4$ system doped with $^{225}Ac$, including at least about 25% by mole of lanthanum in the core resulted in a release of $^{225}Ac$ that was an order of magnitude lower than for a $GdPO_4$ core. In particular, $GdPO_4$ core particles released about 0.96% of the $^{225}Ac$ included therein whereas for $\{La_{0.5}Gd_{0.5}\}PO_4$ core particles released about 0.031% of the $^{225}Ac$ included therein. Alternatively, it may be desirable to select europium in certain applications because europium does not product a large magnetic moment but it is close in size to gadolinium. Regardless of the combination of lanthanides that are selected for inclusion, it is believed that it will be preferable, in terms of $^{225}Ac$ retention, for the mole fraction of lanthanum in the core to be at least about 25% by mole of the lanthanides.

Additionally, it may be desirable, for example, to select one or more lanthanides that aid in the manufacture and/or use of the nanoparticles. For example, gadolinium may be selected for inclusion in the core and/or sequestration shell to impart magnetic properties, which may be useful for separating the nanoparticles from other materials or compounds or for allowing the particles to provide a diagnostic function. But it has been observed that including gadolinium, at least at certain amounts, may actually reduce the ability of a core particle to retain radionuclides.

Still further it may be desirable to select from the aforementioned lanthanide elements those that have β-emitting radioisotopes (e.g., $^{147}Nd$, $^{149}Pm$, $^{151}Pm$, $^{153}Sm$, $^{161}Tb$, $^{166}Ho$, $^{177}Lu$) for inclusion in the core and/or the sequestration shell in order to provide additional therapeutic and/or diagnostic benefits (e.g., mixed alpha-beta therapy).

Although no specific amount of any particular lanthanide in relation to the other such lanthanides that may be present in the core is believed to be required, it is not unusual for any such lanthanides present to comprise at least about 5% by mole of Ln. In fact, it is not unusual for any such lanthanides present to comprise at least about 10, 15, 20, or even 25% by mole of Ln. Conversely, it is not unusual for a lanthanide that is selected to be present to be at an amount such that it comprises up to about 50, 55, 60, 65, 70, 75, 80, 85, 90, or 95% by mole of Ln.

In view of the possible lanthanides and the possible combinations thereof and the possibility of varying the relative amounts of the various lanthanide elements, a large number of embodiments of the present invention in which the core comprises different compositions of lanthanide phosphates may be envisioned. One such embodiment is that Ln comprises lanthanum. In an embodiment, the lanthanum is at an amount that is at least about 25% by mole of Ln. In an embodiment, the lanthanum is at an amount that is no more than about 75% by mole of Ln. In other embodiments, the lanthanum is at an amount that is in the range of about 25 to about 75% by mole of Ln, a range of about 40 to about 60% by mole of Ln, or range of about 45 to about 55% by mole of the Ln. In an embodiment, lanthanum is at an amount that is about 50% by mole of Ln. In an embodiment, Ln is lanthanum.

In an embodiment, Ln comprises gadolinium. In an embodiment, the gadolinium is at an amount that is at least about 25% by mole of Ln. In an embodiment, the gadolinium is at an amount that is no more than about 75% by mole of Ln. In other embodiments, the gadolinium is at an amount that is in the range of about 25 to about 75% by mole of Ln, a range of about 40 to about 60% by mole of Ln, or range of about 45 to about 55% by mole of the Ln. In an embodiment, gadolinium is at an amount that is about 50% by mole of Ln. In an embodiment, Ln is gadolinium.

In an embodiment, Ln comprises lanthanum and gadolinium. In another embodiment, Ln is lanthanum and gadolinium. In embodiments of either of the immediately preceding scenarios, the lanthanum is at an amount that is at least about 25% by mole of Ln and the gadolinium is at an amount that is at least about 25% by mole of Ln. In other embodiments, each of the lanthanum and the gadolinium is at an amount that is in the range of about 25 to about 75% by mole of Ln, a range of about 40 to about 60% by mole of Ln, or range of about 45 to about 55% by mole of the Ln. In an embodiment, each of the lanthanum and the gadolinium is at an amount that is about 50% by mole of Ln.

As mentioned above, the α-emitting-radioisotope-doped $LnPO_4$ comprises an α-particle emitting radioisotope that is selected from the group consisting of $^{225}Ac$, $^{223}Ra$, any radioactive decay products thereof, and combinations thereof. In an embodiment, the α-particle emitting radioisotope is selected from the group consisting of $^{225}Ac$ and its radioactive decay products. The $^{225}Ac$ radioisotope is believed to be a particularly desirable because it produces four α particles in its radioactive decay, wherein its daughter radioactive decay products are $^{221}Fr$, $^{217}At$, $^{213}Bi$, $^{213}Po$, $^{209}Tl$ and $^{209}Pb$. Further, $^{225}Ac$ is desirable as it is readily incorporated into the $LnPO_4$ crystallographic structures at least in part because of its similar size. $^{223}Ra$ is desirable because it also produces four α particles in its radioactive decay, wherein its daughter radioactive decay products are $^{219}Rn$, $^{215}Po$, $^{211}Pb$, $^{211}Bi$, and $^{207}Tl$. Further, $^{223}Ra$ is desirable as it is more readily available than $^{225}Ac$ for targeted alpha therapy.

In an embodiment, the α-emitting-radioisotope-doped $LnPO_4$ is $\{La_{0.25\text{-}0.75}Gd_{0.25\text{-}0.75}\}(^{225}Ac)PO_4$. In another embodiment, the α-emitting-radioisotope-doped $LnPO_4$ is $\{La_{0.40\text{-}0.60}Gd_{0.40\text{-}0.60}\}(^{225}Ac)PO_4$. In yet another embodiment, the α-emitting-radioisotope-doped $LnPO_4$ is $\{La_{0.45\text{-}0.55}Gd_{0.45\text{-}0.55}\}(^{225}Ac)\}PO_4$. In still another embodiment, the α-emitting-radioisotope-doped $LnPO_4$ is $\{La_{0.50\text{-}0.50}Gd_{0.50\text{-}0.50}\}(^{225}Ac)$ $PO_4$.

The amount of α-particle emitting radioisotope that is doped into the $LnPO_4$ may be selected essentially as desired for the particular therapeutic or diagnostic use for the nanoparticles of the present invention are to be subjected. In an embodiment, the α-particle emitting radioisotope is at an amount that is up to about 2,000 ppm of the α-emitting-radioisotope-doped $LnPO_4$. In an embodiment, the α-particle emitting radioisotope is at an amount that is up to about 200 ppm of the α-emitting-radioisotope-doped $LnPO_4$.

Sequestration Shell

As indicated above, the nanoparticles of the present invention comprise a sequestration shell enclosing the core that comprises $LnPO_4$ and is free of an α-emitting-radioisotope and that allows at least some of the α emissions from the α-emitting radioisotope to pass therethrough and prevents at least some radioactive decay products of the α-emitting radioisotope from exiting the α-particle emitting nanoparticle. The Ln represents lanthanide elements selected from the group consisting of La, Gd, Sm, Eu, Tb, Dy, Ho, Lu, Nd, and combinations thereof. It is to be noted that the Ln of the sequestration shell is separately selectable from the Ln of the core. Thus, the particular lanthanide or lanthanides selected for inclusion in the sequestration shell may be the same or may be different from those selected for inclusion in the core. In an embodiment, the sequestration shell consists of $LnPO_4$.

In an embodiment, the sequestration shell has a thickness that is in the range of about 1 nm to about 10 nm. In an embodiment, the sequestration shell has a thickness that is in the range of about 1 nm to about 10 nm. In an embodiment, the sequestration shell has a thickness that is in the range of about 1 nm to about 5 nm.

Although the sequestration shell may be deposited in a single layer, it is typical for a sequestration shell to be made up of a multiplicity of layers (e.g., up to 5 layers), and the Ln of each sequestration shell layer is separately selectable. Typically, each sequestration shell layer has a thickness that is in the range of about 0.2 nm to about 2 nm. In general, the retention of radionuclides tends to increase with increasing numbers of layers. That said, there is a practical limit to the number of layers in that when the sequestration shell reaches a certain thickness the particles tend to no longer remain dispersed in the solution(s) used to deposit the layers. For example, it has been observed that $LaPO_4$ core particles synthesized using an aqueous solvent exhibited the ability to retain about 60% of the $^{221}Fr$ daughter radionuclides, adding two sequestration shell layers of $LaPO_4$ synthesized using an aqueous solvent increased the retention of $^{221}Fr$ to about 70% and adding four sequestration shell layers of $LaPO_4$ further increased $^{221}Fr$ retention to about 80% and even greater. In an embodiment, the number of sequestration shell layers is 4.

As mentioned above, the selection of the Ln for the core and the sequestration shell and even individual layer of the sequestration shell are separately selectable. Notwithstanding, it is presently believed that it is desirable (at least in terms of the retention of retaining radionuclides) to select lanthanides for the sequestration shell such that the resulting $LnPO_4$ layer being deposited has a crystal phase that is similar or identical to the crystal phase of the core or the immediately preceding layer (as the case may be). It has been observed that for $LaPO_4$ core particles, which typically have a rhabdophane crystal phase, it is desirable for the sequestration shell layers to be $LaPO_4$. On the other hand, it has been observed that $\{La_{0.5}Gd_{0.5}\}PO_4$ and $GdPO_4$ both have an anhydrous monazite crystal phase and therefore either of such lanthanide phosphates may be used as the core particles, sequestration shells, or both. For example, it has been observed that using four layers of $LaPO_4$ to encapsulate $\{La_{0.5}Gd_{0.5}\}PO_4$ cores doped with $^{225}Ac$ resulted in about 80% retention of $^{221}Fr$ whereas using four layers of $GdPO_4$ increased the $^{221}Fr$ retention to about 90%. Without being held to a particular theory, it is presently believed that lanthanide phosphates comprising one or more of samarium, terbium, dysprosium, holmium, and lutetium are likely to have a crystal phase that is a better match for $\{La_{0.5}Gd_{0.5}\}PO_4$ and $GdPO_4$ and may result in even higher degrees of radionuclide retention.

In an embodiment, the Ln of the sequestration shell is lanthanum, including all the layers thereof. In an embodiment, the Ln of the sequestration shell is gadolinium, including all the layers thereof. In an embodiment, the Ln is a combination of lanthanum and gadolinium. In an embodiment, the core particles comprise anhydrous monazite $\{LaGd\}PO_4$ (e.g., $\{La_{0.5}Gd_{0.5}\}PO_4$) and the sequestration shell comprises four layers of anhydrous monazite $GdPO_4$. Notwithstanding the difference in crystallographic structure, in an embodiment, the core particles comprises anhydrous monazite $\{La_{0.5}Gd_{0.5}\}PO_4$ and the sequestration shell comprises rhabdophane $LaPO_4$.

In view of the foregoing, in embodiments of the present invention, the core particles as disclosed may be made that are able to retain more than 50%, or at least about 60% of one or more daughter radionuclides and with the addition of the sequestration shell the retention of one or daughter radionuclides may be increased to at least about 70, 80, 90% or even greater.

Making Cores and Sequestration Shells

The α-particle emitting cores may be formed by treating a core solution, which comprises $Ln^{3+}$ anions, α-emitting-radioisotope ions, and $PO_4$-containing anions, to cause the reaction of $Ln^{3+}$ cations and $(PO_4)^{3-}$ anions thereby forming the α-particle emitting cores.

Similarly, the sequestration shells may be formed by treating a colloidal suspension that comprises particles, which comprise the α-particle emitting cores and any previously deposited layers, if any, dispersed in a shell solution, which comprises $Ln^{3+}$ cations and $PO_4$-containing anions, to cause the reaction of $Ln^{3+}$ cations and $(PO_4)^{3-}$ anions thereby resulting in the formation of one such layer on the particles. One would repeat the foregoing treatment until the desired number of layers is deposited.

More specifically, the cores and the sequestration shells nanoparticles may be made by a method that is in general accordance with a methodology described by Buissette et al. (Colloidal Synthesis of Luminescent Rhabdophane LaPO: Ln.xHO (Ln=Ce, Tb, Eu; x≈0.7) Nanocrystals, Buissette et al. *Chem. Mater.* 2004, 16, 3767-3773; Luminescent Core/Shell Nanoparticles with a Rhabdophane $LnPO_4$-$xH_2O$ Structure: Stabilization of $Ce^{3+}$-Doped Compositions, Buissette et al., *Adv. Funct. Mater.* 2006, 16, 351-355; Aqueous routes to lanthanide-doped oxide nanophosphors, Buissette et al., *J. Mater. Chem.,* 2006 16, 529-539; and U.S. Pub. No. 20070131906 (U.S. Ser. No. 10/572,299) each of which is incorporated by reference herein in its entirety). That said it is to be noted that although Buissette et al. only disclose using tripolyphosphate as a source for $PO_4$-containing anions, monophosphates and diphosphates may also be sources for such anions in addition to other larger polyphosphates. In general, all other things being equal, as the amount of smaller phosphates used as a source of $PO_4$-containing anions increases the diameter and thickness of cores and shell layers, respectively, tend to increase. Without being held to a particular theory, it is believed that this effect on thickness is due, at least in part, to the fact that larger polyphosphates take a longer time to react. Further, it is believed that tripolyphosphate provides a good balance between reasonable reaction speed and particle size. The solution is heated to cause the hydrolysis of at least some of the $PO_4$-containing anions of the tripolyphosphate thereby breaking it into diphosphate and monophosphate. The monophosphate is incorporated into the particle while the remaining tripolyphosphate caps the growth by generating a sufficient negative charge to induce electrostatic repulsion and prevent aggregation into larger particles. In an embodiment, a source of the $PO_4$-containing anions is selected from the group consisting of monophosphates, diphosphates, polyphosphates, and combinations thereof. In an embodiment, source of the $PO_4$-containing anions is one or more tripolyphosphates.

Briefly, the methodology for forming $LnPO_4$ nanoparticle cores which also comprise the dopant, and sequestration shells involves treating the aforementioned core solution and shell solution both of which comprises the Ln cations and $PO_4$-containing anions. Typically, these core and shell solutions are formed by mixing one or more solutions comprising an aqueous solvent and one or more of Ln-containing salts (e.g., $LaCl_3$ and $GdCl_3$) and one or more solutions comprising $PO_4$-containing salts (e.g., sodium tripolyphosphate) anions. The reaction of the $Ln^{3+}$ cations and $(PO_4)^{3-}$ anions is caused by treating the core solution or the shell solution, for example, by controlling the pH and/or temperature thereof for a desired duration thereby forming the α-particle emitting cores or a sequestration shell, as the case may be. As is evident, when forming the cores the core solution also comprises α-emitting-radioisotope ions that are usually sourced from salts of the same such as chloride, bromide, iodide, and/or nitrate salts. Further, when forming sequestration shell layers the cores are dispersed in the shell solution and a part of the aforementioned colloidal suspension.

It has been observed that core particle size depends, at least in part, on the duration at which the particular solution is held at the appropriate pH and/or temperature for facilitating the reaction between the lanthanide and phosphate ions. More specifically, it has been observed that, all things being equal otherwise, particle size tends to increase with duration and that particles having a diameter in the range of about 5 to about 7 nm may be produced using a duration that is typically in the range of about 4 to about 5 hours. In an embodiment, the treating of the colloidal suspension to cause to cause the reaction of $Ln^{3+}$ cations and $(PO_4)^{3-}$ anions comprises controlling the temperature of the suspension such that it is in the range of about 60 to about 100° C. for a duration that is in the range of about 1 to about 5 hours. In an embodiment, the treating of the colloidal suspension to cause the reaction of $Ln^{3+}$ cations and $(PO_4)^{3-}$ anions comprises controlling the temperature of the suspension such that it is in the range of about 85 to about 95° C. for a duration that is in the range of about 2 to about 4 hours.

Further, it has been observed that the selection of the solvent may be used to affect the ability of the core particles and the sequestration shell to retain radionuclides. Specifically, it has been found that the selection of the solvent may affect the diameter of the core particles and/or the thickness of sequestration shell layers, which affects the degree of radionuclide retention. For example, $LaPO_4$ particles synthesized in an organic solvent mixture containing tri-n-butyl phosphate, phenyl ether, and tri-n-octylamine exhibited the ability to retain about 50% of the $^{221}Fr$ daughter in vitro. In contrast, $LaPO_4$ particles synthesized in aqueous solvent exhibited about 60% retention of the $^{221}Fr$ daughter.

In an embodiment, for the core solution the $Ln^{3+}$ ions are at an amount that is in the range of about 0.01 M to about 1 M in the core solution, $PO_4$-containing anions are tripolyphosphate ions that are at an amount that is in the range of about 0.02 M to about 2 M in the core solution, the ratio of $Ln^{3+}$ ions to tripolyphosphate ions is in the range of about 2:1 to about 1:4, and the α-emitting-radioisotope ions are at an amount up to 100 mCi in the core solution. In an embodiment, for the core solution the $Ln^{3+}$ ions are at an amount that is in the range of about 0.02 M to about 0.2 M in the core solution, the $PO_4$-containing anions are tripolyphosphate ions that are at an amount that is in the range of about 0.04 to about 0.4 M in the core solution, the ratio of $Ln^{3+}$ ions to tripolyphosphate ions is in the range of about 1:1 to about 1:2, and the α-emitting-radioisotope ions are at an amount up to about 10 mCi of the core solution.

In an embodiment, for the shell solution the particles are at an amount that is in the range of about 0.1 mg/mL to about 50 mg/mL of the colloidal suspension, the $Ln^{3+}$ cations are at an amount that is in the range of about 0.005 M to about 0.5 M in the shell solution, the $PO_4$-containing anions are tripolyphosphate ions that are at an amount that is in the range of about 0.01 M to about 1 M in the shell solution, and the ratio of $Ln^{3+}$ cations to tripolyphosphate ions is in the range of about 2:1 to about 1:4. It is to be noted that, the mass of the particles in the colloidal suspension tends to increase with each shell layer being added in that it is typical (but not required) for the reaction volume to be maintained relatively constant but the particles dispersed therein become heavier for each layer added. For example, a colloidal suspension comprising the initial cores, the cores may comprise about 4 mg/mL of the colloidal suspension and each shell addition may add another about 4 mg/mL to the particles so at the beginning of adding a fifth layer the particles would comprises about 20 mg/mL of the colloidal suspension and after the completion of the fifth layer the particles would comprises about 24 mg/mL of the colloidal suspension. In an embodiment, the particles are at an amount that is in the range of about 1 mg/mL to about 30 mg/mL of the colloidal suspension, the $Ln^{3+}$ cations are at an amount that is in the range of about 0.01 M to about 0.1 M in the shell solution, the $PO_4$-containing anions are tripolyphosphate ions that are at an amount that is in the range of about 0.02 M to about 0.2 M in the shell solution, and the ratio of $Ln^{3+}$ cations to tripolyphosphate ions is in the range of about 1:1 to about 1:2.

The preparation of the particles, the cores or the core plus shells may be separated or purified from other solution components by any appropriate method such as by dialysis, filtration, chromatography, centrifugation, or in the even by application of a magnetic field if a magnetic lanthanide were included therein.

Outer Coating

Additionally, in an embodiment of the present invention the α-particle emitting nanoparticle further comprises an outer coating deposited on the sequestration shell, wherein the outer coating comprises gold. In an embodiment, the outer coating has a thickness that is in the range of about 1 nm to about 60 nm. In an embodiment, the outer coating has a thickness that is in the range of about 2 nm to about 25 nm. In general, increasing the thickness of the gold also enhances the retention of radionuclides within the nanoparticles. In an embodiment the outer coating consists of gold. In an embodiment, the gold of the outer coating comprises one or more of the following gold isotopes $^{199}Au$, $^{198}$ Au, and $^{197}Au$.

Such a gold-containing outer coating provides several benefits such as the fact that chemical reactions on gold surfaces occur relatively easily and quickly under relatively mild conditions, gold surfaces are relatively inert and tend to remain unreactive under biological conditions (e.g., in a body), gold surfaces are readily functionalized so that the particles may be imparted with a relatively high degree of solubility and the ability to target specific types of tissue or locations in a body. In particular, citrate and polyethylene glycol (PEG) coating added to the gold-containing outer coating impart much higher degrees of water solubility to the particles compared to particles having a $LnPO_4$ outer surface.

Making Outer Coatings

Additionally, the present invention is directed to a method of enclosing nanoparticles having $LnPO_4$ surfaces with shells comprising gold. The method comprising treating a mixture comprising the nanoparticles dispersed in a gold-containing solution comprising solute gold ions and citrate ions solution to reduce the solute gold ions such that at least some of the reduced gold comes out of solution and deposits on the surfaces of the nanoparticles thereby forming the shells. Importantly, it has been discovered that in order to coat the nanoparticles with gold such that an outer coating is depositing on individual particles is formed rather than forming aggregated gold nanoparticles, the conditions used to layer the gold are fairly specific. In particular, it has been discovered to form the desired gold coated $LnPO_4$ nanoparticles, the ratio of gold to nanoparticles to citrate is preferably controlled. For example, it has been observed that if there is too much gold, free gold nanoparticles tend to form and they tend to form aggregates and settle out of solution. On the other hand, if there is too little gold, there is not enough to coat the particles. In particular it has been observed that about 1 mg of $LnPO_4$ particles are coated well with about 2.5 μmol $AuCl_4^-$ and about 30 μmol of trisodium citrate. It is believed that deviating from this ratio by an order of magnitude or more in any direction tends to result in either aggregated gold particles or inadequately coated $LnPO_4$ nanoparticles.

In an embodiment, the mixture is, was, or has been formed (by the entity performing the method or a different entity) by mixing a particle solution comprising the particles and the citrate ions and a gold-containing solution, and wherein the gold is at an amount that is in the range of about 0.1 mM to about 10 mM in the gold-containing solution, the citrate is at an amount that is in the range of about 0.001 M to about 0.1 M of the particle solution, the particles are at an amount that is in the range of about 0.1 mg/mL to about 10 mg/mL of the mixture, and the mass ratio of solute gold to particles to citrate in the mixture is about 0.6-60:0.1-10:1.2-120. In an embodiment, the reduction of the gold ions comprises controlling the temperature of the mixture such that it is in the range of about 50 to about 100° C. for a duration that is in the range of about 0.3 to about 3 hours.

In an embodiment, the mixture is, was, or has been formed (by the entity performing the method or a different entity) by mixing a particle solution comprising the particles and the citrate ions and a gold-containing solution, and wherein the gold is at an amount that is in the range of about 0.5 mM to about 5 mM in the gold-containing solution, the citrate is at an amount that is in the range of about 0.005 M to about 0.05 M in the particle solution, the particles are at an amount that is in the range of about 0.5 mg/mL to about 5 mg/mL in the mixture, and the mass ratio of solute gold to particles to citrate in the mixture is about 3-9:0.5-2:6-18. In an embodiment, the reduction of the gold ions comprises controlling the temperature of the mixture such that it is in the range of about 70 to about 95° C. for a duration that is in the range of about 0.5 to about 1.5 hours.

Advantageously, including a magnetic lanthanide such as gadolinium in the core and/or shell allows for the gold coated nanoparticles to be separated magnetically from other things such as free gold nanoparticles. While the magnetic moment of the gadolinium is low, it is sufficient to separate the layered particles from non-layered gold co-reduced in solution. By removing such free gold nanoparticles, it can be ensured that they do not compete for receptor sites in vivo. Thereby potentially allowing for relatively low concentrations of the radioactive nanoparticles, as each targeted particle will contain therapeutic radionuclide. Measurements with $^{225}$Ac as a tracer indicated that 72% of the particles with four $GdPO_4$ shells separate out of solution next to the magnet after a 16 hour period. Longer separation times improve separation efficiency, but at the cost of activity. Additionally, the nanoparticles may be able to be directly localized using magnetic fields (see, e.g., Schillinger, U.; Brill, T.; Rudolph, C.; Huth, S.; Gersting, S.; Krotz, F.; Hirschberger, J.; Bergemann, C.; Plank, C. *J. Magn. Magn. Mater.* 2005, 293, 501).

Surface Functionalization Component

For nanoparticles of the present invention that comprise the above-described gold-containing outer coating, one may capitalize on the extensive methods known in the art for gold surface functionalization there by allowing for a versatile system for clinical α radiation delivery to various targets in vivo. As set forth below, proof of principle was demonstrated using mAb 201B to deliver a therapeutic payload of $^{225}$Ac to lung tissue in vivo with receptor specific uptake and vascular targeting. As such, in an embodiment the α-particle emitting nanoparticle may further comprise a surface functionalization component adhered to the outer coating. In an embodiment, the surface functionalization component comprises a linker component and target component. Without intending to limit, exemplary linkers include a lipoamide-PEG-acid, a lipoamide-PEG-amine, a lipoic acid-PEG-biotin, lipoic acid-PEG-N hydroxy succinimide, thio-PEG-N hydroxyl succinimide, thiol-PEG-Acid, thiol-PEG-amine, and combinations thereof. Also without intending to limit, exemplary target components include antibodies (e.g., mAb 201b, panitumumab, cetuximab), aptamers, biotin, peptides, and small molecule cancer targeting agents (e.g., octreotide and lanreotide).

Uses of α-Particle Emitting Nanoparticles

Nanoparticles inherently possess a number of favorable properties with regard to drug delivery. The ability to hold multiple copies of a therapeutic or imaging moiety provides the ability to generate efficacious results even against targets with low receptor numbers in vivo (McDevitt, M. R., Sgouros, G., Finn, R. D., Humm, J. L., Jurcic, J. G., Larson, S. M., and Scheinberg, D. A. *Eur. J. Nucl. Med.* 1998, 25, 1341-1351). Multi-functional, layered nanoparticles allow for synergistic combinations of properties exhibited by the individual nanoparticles for myriad applications including nuclear medicine, luminescence, catalysis, and many more (see, e.g., Oku, T.; Nakayama, T.; Kuno, M.; Nozue, Y.; Wallenberg, L. R.; Niihara, K.; Suganuma, K. *Mat. Sci. Eng. B* 2000, 74, 242; Feng, H.; Lu, J.; Stair, P. C.; Elam, J. W. *Catal. Lett.* 2011, 141, 512). In view of this, a person of skill in the art will readily appreciate that one or more of the various embodiments of the α-particle emitting nanoparticles of the present invention may be well suited for in vivo therapeutic and/or diagnostic uses (e.g., imaging functionality) because, for example, $GdPO_4$ can function as an MRI contrast agent, gold may be doped with the SPECT radionuclide $^{199}$Au for gamma imaging.

Thus, the present invention is also directed to a composition for targeted in vivo generated alpha radiotherapy, wherein the composition comprises phosphate buffered saline and a multiplicity of α-particle emitting nanoparticles as described above. Still further, the present invention is directed to a method for conducting targeted in vivo generated alpha radiotherapy, wherein the method comprises administering to a patient an effective amount of said composition. In view of known treatments for metastatic bone cancer using $^{223}$Ra, it is anticipated that in an embodiment of the composition for targeted in vivo generated alpha radiotherapy the composition would be administered on the order of 50 to 250 kBq/kg.

β-Particle Emitting Radioisotope

It is to be noted that the present invention also is directed to embodiments in which the nanoparticles do not comprise any α-particle emitting radioisotope in the core but comprise β-particle emitting radioisotope in the core and/or the sequestration shell. In such an embodiment, the nanoparticles need not comprise a sequestration shell free of β-particle emitting radioisotope or even a sequestration shell at all for that matter because the retention of radionuclides with respect to β-particle emitting radioisotopes is not of particular concern. In such an embodiment, the nanoparticles would comprise a β-particle emitting core that comprises a β-emitting-radioisotope-doped $LnPO_4$, wherein some portion of the Ln is a β-particle emitting radioisotope is selected from the group consisting of $^{147}$Nd, $^{149}$Pm, $^{151}$Pm, $^{153}$Sm, $^{161}$Tb, $^{166}$Ho, $^{177}$Lu, and combinations thereof. The core may be covered in a coating comprising gold that may be functionalized as set forth above. Further, such β-particle emitting nanoparticles may be included in compositions for therapeutic and/or diagnostic uses.

EXAMPLES

Example 1

The example is directed to demonstrating that α emitting nanoparticles of the present invention comprising a gold outer coating and functionalized using mAb 201B may be used to deliver a therapeutic payload of $^{225}$Ac to lung tissue in vivo with receptor specific uptake and vascular targeting.

Experimental

All chemicals were used as received from Sigma-Aldrich and were at least ACS grade unless noted. Water originated from an in-house MILLIQ system. $^{225}AcCl_3$ was prepared as described by Woodward et al. (Woodward, J.; Kennel, S. J.; Stuckey, A.; Osborne, D.; Wall, J.; Rondinone, A. J.; Standaert, R. F.; Mirzadeh, S. *Bioconj. Chem.* 2011, 22, 776). The radioactivity measurements were performed as described by Woodward et al.

Preparation of $\{La_{0.5}Gd0_{.5}(^{225}Ac)\}PO_4$ Core Nanoparticles

Core particles were made by modifying a methodology disclosed by Buissette et al. Briefly, 50 μL each of 0.1 M $LaCl_3$ and $GdCl_3$ were mixed in a 1 mL V-bottom vial with spin vane. For the radioactive nanoparticles production, 5.2 mCi of $^{225}AcCl_3$ in 0.1 M HCl was added to the lanthanide mixture. Next, 200 μL of 0.1 M sodium tripolyphosphate (Na-TPP) was added to give a total Ln:Na-TPP ratio of 1:2 resulting in a clear, colorless solution. If the solution remained turbid after addition of Na-TPP, it was vortexed with small additions of Na-TPP until the solution appeared clear. The resulting solution was then capped and heated at about 90° C. for about 3 hours giving a turbid, white suspension of particles. Particles were purified via dialysis overnight against 18 MΩ water in a Spectra/Por 10,000 Da molecular weight cutoff regenerated cellulose membrane (washed of preservatives before use) against 18 MΩ water. This preparation produced monodisperse particles of approximately 4 nm diameter that were characterized by transmission electron microscopy (TEM), neutron activation analysis (NAA) and x-ray diffraction (XRD).

Preparation of Sequestration Shell

Core particles described above were centrifuged at about 3,000 g for about 3 minutes and the supernatant was removed. The particles were re-dispersed in a solution consisting of 67 μL of 0.05 M $GdCl_3$ and 133 μL 0.05M Na-TPP. The total volume of this liquid was twice the volume used to make the core particles. The resulting mixture was vortexed briefly then sonicated using a bath sonicator for about 10 minutes before heating at about 90° C. for about 3 hours. This process was repeated for up to four shell additions, at which point the solution becomes a thick milky white. Particles were purified by dialysis as above before gold coating.

About 12 mg of dialyzed particles were collected and split evenly between three 5 mL V-bottom vials. About 300 μL of 0.1 M tribasic sodium citrate was added to each vial along with about 1.5 mL of 18 MΩ water. Next, about 2.5 mL of 1 mM $NaAuCl_4^-$ was added dropwise to the solution slowly at the rate of about 1 mL every 10 minutes. After the final addition, the solution was kept at about 90° C. for a duration between about 30 and about 45 minutes. A large NdFeB magnet (surface field>0.3 T) was placed next to the V-bottom vial for about 16 hours to separate the particles from solution. The supernatant was decanted to isolate the magnetically active particles.

In Vitro Testing of $^{221}$ Fr

In order to test retention of the $^{225}$Ac decay products in vitro, the $^{225}$Ac-nanoparticles were loaded into a 10,000 MWCO regenerated cellulose dialysis membrane and dialyzed against 400 mL of 18 MΩ water. The dialysis tube was stirred for a sufficient time for daughter equilibrium to be established (>3 hours), then a 5 mL aliquot was taken for gamma-ray spectrometry analysis. Each sample was re-analyzed at a later time to determine the level of $^{225}$Ac in the removed dialysate fraction. The measured activities were corrected for decay and dialysate loss from prior aliquot removals. Because previous experiments showed that $^{213}$Bi which escaped from the particles did not move across the dialysis membrane, the $^{213}$Bi activity in the dialysate was used as a measure of the $^{221}$Fr that was released from the nanoparticle.

Surface Modification

Surfaces were modified using a lipoamide-$dPEG_{12}$-acid linker (Quanta Biodesign). About 2 mg of dPEG were added, followed by about 6 mg of Tris(2-carboxyethyl)phosphine reducing agent to cleave the disulfide bond. The pH of the solution was adjusted to about 7 using dilute NaOH and the reaction mixture was stirred for about 4 hours. Connection of the linker was determined by a shift in the plasmon resonance as monitored by UV-Vis spectroscopy before and after the addition of the linker.

Antibody Conjugation

Antibodies were conjugated to the particles using established procedures from the scientific literature (Wang S P, Mamedova N, Kotov N A, Chen W and Studer J 2002 Nano Lett. 2 817-22). Aqueous solutions of 3-sulfo-N-hydroxysuccinimide (sulfo-NHS) and 1-ethyl-3-(3-dimethylaminopropyl)-carbodiimide (EDC) were added to activate the protein and carboxyl group for reaction. The carboxylate group was first activated using about 8 μL of 10 mg/mL aqueous 3-sulfo-N-hydroxysuccinimide (sulfo-NHS) and about 80 μL of 1-ethyl-3-(3-dimethylaminopropyl)-carbodiimide (EDC). About 4 mg of EDC and about 0.4 mg of sulfo-NHS were used per mg of nanoparticles. The particles were then centrifuged to remove excess EDC/NHS, the supernatant was removed, and the particles were re-dispersed in phosphate buffered saline (PBS) (0.01 M $NaPO_4$ pH 7.6 in 0.15 M NaCl). The mAb 201B was added (~1 mg of mAb/mg of NP) and the mixture was stirred overnight. The reaction was then quenched with about 1 mg of glycine, which was allowed to react for 15 minutes. The particles were then centrifuged to remove excess antibody. The supernatant was removed and the particles were re-dispersed in PBS containing about 5 mg/mL bovine serum albumin (BSA/PBS). The particles were sonicated with a Branson microprobe for about 10 sec and vortexed prior to injection. The final product of the mAb conjugated nanoparticles was ~3 mg/mL nanoparticles with about 400 μCi of Ac-225 and ~1 mg mAb 201B. It is noted that mAb 201b has previously been used successfully for proof of principle targeting of nanoparticles in vivo (Woodward, J. D.; Kennel, S. J.; Mirzadeh, S.; Dai, S.; Wall, J. S.; Richey, T.; Avenell, J.; Rondinone, A. J. *Nanotechnology,* 2007, 18, 175103).

Biodistribution Studies

Female BALB/c mice (body mass ~20 g) were used for all biodistribution and imaging experiments. Biodistribution and daughter retention assays were done on three groups, consisting of three mice per group, were each injected intravenously (tail vein). Groups 1 and 2 were injected with $Au/GdPO_4/\{La_{0.5}Gd_{0.5}(^{225}Ac)\}PO_4$-mAB-201b outer coating/sequestration shell/core conjugates, while group 3 was treated with $Au/GdPO_4/\{La_{0.5}Gd_{0.5}(^{225}Ac)\}PO_4$-PEG as a control. The group 1 mice received 14.6 μg of nanoparticles with about 1.95 μCi of $^{225}$Ac and ~5 μg of attached mAb 201B (this value was estimated from data in a parallel experiment wherein about 30% of added radioiodinated mAb was incorporated in nanoparticles under similar conditions). The group 2 mice received the same amount of targeted nanoparticles but with the addition of about 750 μg of free mAb 201B as competitor. The group 3 mice received the same amount of nanoparticles and $^{225}$Ac but with no targeting agent conjugated. The mice were housed with food and water ad libitum in a light/dark cycle environment before sacrificing at 1 hour and 24 hours postinjection for biodistribution and in vivo retention studies. Biodistribution studies were performed on lungs, liver, spleen, and kidneys to evaluate the amount of both $^{221}$Fr and $^{213}$Bi in target organs by measuring weighed tissue samples in a γ-ray scintillation counter at a specific time post-sacrifice and again after the radioisotopes had achieved decay equilibrium (>3 h). The quantities of $^{221}$Fr and $^{213}$Bi present at the time of animal sacrifice were determined by appropriate crossover and decay corrections as previously described by Woodward et al. (Woodward, J.; Kennel, S. J.; Stuckey, A.; Osborne, D.; Wall, J.; Rondinone, A. J.; Standaert, R. F.; Mirzadeh, S. *Bioconj. Chem.* 2011, 22, 776).

Results

A Rietveld refinement was used to calculate the size of the particle cores for the various combinations of lanthanum/gadolinium, which are shown in Table 1, below. The $LaPO_4$ nanoparticles exhibited the rhabdophane phase consistent with the description of Buissette et al. but the $\{La_{0.5}Gd_{0.5}\}PO_4$, $\{La_{0.25}Gd_{0.75}\}PO_4$, and $GdPO_4$ systems crystallized in the anhydrous monazite phase (see Meiser, F.; Cortez, C.; Caruso, F., *Angew. Chem.-Int. Edit.* 2004, 43, 5954). The monazite phase for $LaPO_4$ was previously observed for crystalline synthesis in organic solvents. Presumably, the smaller size of the Gd ion decreased the free space available in the crystal, causing water elimination in the combined system. Further, the doping of the $^{225}$Ac into the crystal structure appeared to disrupt crystal formation. Both pure $LaPO_4$ and pure $GdPO_4$ particles exhibited larger grain sizes than the $\{LaGd\}PO_4$ particles. Further, the particles sizes determined by TEM match that as determined by XRD, which indicates that the core particles are a single crystal phase.

TABLE 1

| Structure | Crystal Phase | Grain Size (nm) |
|---|---|---|
| $LaPO_4$ | Rhabdophane | 4.04 |
| $\{La_{0.5}Gd_{0.5}\}PO_4$ | Monazite | 2.79 |
| $\{La_{0.25}Gd_{0.75}\}PO_4$ | Monazite | 2.91 |
| $GdPO_4$ | Monazite | 3.11 |

The TEM indicated that the gold coating caused an increase in mean particle size from 4 nm to 35 nm. The NAA analysis indicated that the gold:lanthanide ratios were inconsistent with a large shell of gold, therefore multiple $LnPO_4$ particles may be present in a single Au layered particle (Table 2). A control experiment where the layered lanthanide phosphate particles were treated with citrate and heated in the absence of gold failed to induce aggregation, therefore the addition of gold must be the contributing factor in particle growth. The EELS-TEM analysis confirms the presence of La, Gd, and Au in all discrete particles examined.

TABLE 2

| Particle System | Technique | Measurement | Result |
|---|---|---|---|
| $\{La_{0.5}Gd_{0.5}\}PO_4$ Core | NAA | La:Gd ratio | 1.11 +/− 0.03 |
| $Au/GdPO_4/\{La_{0.5}Gd_{0.5}\}PO_4$ | NAA | Au:Ln ratio | 0.423 +/− 0.001 |

The particles were further characterized by dynamic light scattering. Hydrodynamic diameters and zeta potentials are shown in Table 3. Growth of the hydrodynamic diameter on addition of PEG and antibody are common for nanoparticles. The highly negative Zeta potentials should lead to stability in aqueous solution which was confirmed by monitoring the UV-Vis shift of the particles over a 1 month period in both milliq water and saline solution. No shift was observed in the plasmon resonance.

TABLE 3

| Particle | Hydrodynamic Diameter (nm) | Zeta Potential (mV) |
|---|---|---|
| $Au/GdPO_4/\{La_{0.5}Gd0_{.5}(^{225}Ac)\}PO_4$-citrate | 101.4 +/− 1.5 | −63.2 +/− 1.6 |
| $Au/GdPO_4/\{La_{0.5}Gd0_{.5}(^{225}Ac)\}PO_4$-PEG | 382.3 +/− 6.5 | −56.4 +/− .14 |
| $Au/GdPO_4/\{La_{0.5}Gd0_{.5}(^{225}Ac)\}PO_4$-mAB-201b | 1498 +/− 76.9 | −27.9 +/− 2.4 |

In vitro retention results with four epitaxially added $GdPO_4$ sequestration shell layers and a gold outer coating exhibited dramatically increased retention compared with previously published results for core-only lanthanum phosphate particles. The initial retention of the $^{221}$Fr daughter was about 98%. This number decreased by about 2% per day over the course of a week, reaching a plateau at about 88%. As mentioned above, previous work with core-only $LaPO_4$ nanoparticles demonstrated that only 50% of the $^{221}$Fr was retained. Further, the presence of the $Au/GdPO_4$ shells increased the retention of the $^{225}$Ac parent itself by roughly an order of magnitude. Over the course of 3 weeks, the particles consistently contained >99.99% of the $^{225}$Ac parent radionuclide.

The in vivo experiments quantitating the biodistribution of $^{225}$Ac demonstrated that the antibody-targeted particles localized in the lung consistent with the binding properties of mAb 201b as shown in Table 4.

TABLE 4

| Tissue | Avg % ID/g | Std. Dev. |
|---|---|---|
| Liver | 47.52 | 4.68 |
| Spleen | 46.66 | 33.63 |
| Kidney | 5.34 | 0.96 |
| Lung | 151.00 | 35.40 |

The particles exhibited high uptake with the antibody conjugate after one hour (151% D/g) indicating that the antibody retained its binding affinity and specificity even after conjugation to the nanoparticle. When competed with unconjugated antibody, this uptake dropped to 16.8% ID/g, slightly higher than the control PEG functionalized particles (5.73% ID/g). This order of magnitude difference in nanoparticles localized to the lung indicated that the presence of the high targeting efficacy is due to antibody binding.

Clearance of the particles occurs rapidly through the reticuloendothelial system. After about 24 hours, activity is predominantly present in the liver and spleen. Strategies used to reduce reticuloendothelial functioning such as treatment with clodronate liposomes could be applied to mitigate this effect (see, e.g., Kennel, S. J., Woodward, J. D., Rondinone, A. J., Wall, J., Huang, Y., and Mirzadeh, S, *Nucl. Med. Biol.* 2008, 35, 501; Vanrooijen, N. J. *Immunol. Methods* 1989, 124, 1; and Lasbury, M. E.; Durant, P. J.; Ray, C. A.; Tschang, D.; Schwendener, R.; and Lee, C. H. J. *Immunol.* 2006, 176, 6443. In fact, this has been tested and verified by administering about 100 μL of clodronate liposome in conjunction with above-described nanoparticles and the results for % ID in lung are set forth in Table 5.

TABLE 5

| Time post-injection (h) | % ID in clodronate treated mice | % ID in mice without clodronate |
|---|---|---|
| 1 | 20.52 | 13.41 |
| 4 | 16.68 | 7.08 |
| 24 | 13.41 | 2.46 |

The retention of the $^{213}$Bi daughter in vivo was, as expected, lower than that of the $^{221}$Fr daughter. The decays of $^{225}$Ac, $^{221}$Fr, and $^{217}$Bi tend to move the remaining α-emitting nuclides out of the core towards the surface of the particle. From this position nearer the surface, subsequent decays were more likely to kick the parent nuclide free of the particle. Because the $^{213}$Bi daughter is released farther down the decay chain, it is more likely to escape than the $^{221}$Fr daughter. Despite this, as shown in Table 6, the retention of the $^{213}$Bi daughter in lung tissue was about 69% after 1 hour. This value improved to about 84% after 24 hours. Also notable, was that the amount of $^{213}$Bi that relocated to the kidney from other tissues showed a marked reduction with the Au/$GdPO_4$/{$La_{0.5}$Gd0$_{.5}$($^{225}$Ac)}$PO_4$-mAB-201b system. Thus, despite the widespread concern about $^{213}$Bi relocation to the kidney with $^{225}$Ac radiopharmaceutical systems, using nanoparticles of the present invention resulted in only about 2.8% of the injected dose being detected in kidney tissues after about 1 hour. After 24 hours, this number further decreased to 1.5%. These values represent clear improvements over previously reported core-only nanoparticles, which showed about 10% of the $^{213}$Bi relocated to the kidney after 1 hour and about 5% after 24 hours.

TABLE 6

| Tissue | Retention at 1 hr (%) | Retention at 24 hrs (%) |
|---|---|---|
| liver | 80.7 | 91.7 |
| spleen | 71.6 | 82.2 |
| lung | 68.8 | 84.0 |

Larger doses of $^{225}$Ac may be imaged using CT/SPECT of the $^{221}$Fr γ ray (218 keV, 11.6%). Mice injected with these larger doses were sacrificed and imaged three hours later to allow the daughter products to come into equilibrium. These images clearly showed large uptake in the lung for the case of Au/$GdPO_4$/{$La_{0.5}Gd_{0.5}$($^{225}$Ac)}$PO_4$-mAB-201b particles in agreement with the biodistribution data. When competed with non-conjugated mAb 201b antibody, the image showed high uptake in the gut. When the antibody conjugated particles cannot bind their in vivo target, they are cleared from circulation via the reticuloendothelial system. Finally, PEG coated particles without antibody for lung targeting also show high uptake in the reticuloendothelial system, further indicating that the lung uptake is not due to particulate trapping in the small capillary system.

Example 2

The example is directed to demonstrating that α emitting nanoparticles of the present invention comprising a gold outer coating and functionalized or conjugated to biomolecules utilized by nervous tissue may be used to deliver a therapeutic payload of $^{225}$Ac to brain tissue in vivo. In particular, the tumor vasculature of glioma cells were targeted because of their increased permeability compared to the normal blood brain barrier. Thus, it is believed a nanoparticle based α-therapeutic agent would provide a significant leap forward in treatment of glioma with minimal damage to surrounding healthy neurons.

The nanoparticles were prepared in the same manner as set forth in Example 1 except for the functionalization in which antibodies (to either glial fibrillary acidic protein [GFAP] or synaptophysin) were anchored to the surface linker with established EDC/NHS chemical methods. The process was identical to the addition of mAB 201b as described above, including quantities and ratios, except with GFAP or synaptophysin antibody being used.

Murine biodistribution studies were performed by separate intra-peritoneal (IP), and intravenous injections (catheter in the L femoral vein) injections of GFAP and Synaptophysin labeled particles. Brain, tongue, heart, lung, liver, spleen, colon, skin, and bone were harvested as follows: flash frozen 4 hours post IP injection for neutron activation analysis (NAA); 2 hours post IP injection (transthoracic cardiac perfusion fixation (2.18% paraformaldehyde-cacodylate buffer) for NAA, transmission electron microscopy (TEM), and light microscopy (immunohistochemistry and H&E/luxol fast blue), 1 hour post IV injection (IV perfusion fixation as above). Six hundred samples were obtained for study from twenty animals.

Conclusion

Compared with single α emitting therapies, the use of the present in vivo α generators holds the potential to deliver a much larger biologically effective dose to target tissues. An effective design of in vivo radiopharmaceutical generator systems such as $^{225}$Ac requires two major components. First, the therapeutic must be able to deliver the generator radionuclide dose specifically to target tissue and in a high enough concentration to induce a cell kill. The high uptake of the nanoparticles of the present invention in the lung demonstrates the ability to deliver the system to desired tissue targets. Second, the therapeutic must be able to retain the daughter products of the decay in the target tissue. If the daughter products escape and migrate to non-target tissue, all the advantages of targeted alpha therapy become neutralized. As demonstrated, nanoparticles of the present invention have the ability to retain a significant portion of daughter products such that it is believed they are suitable for effective clinical use.

Additionally, the ability to limit the toxic effects of radiation therapy on normal brain tissues and cells is an important goal in treating brain tumors. Linking a short path length α-emitting radionuclide such as $^{225}$Ac to a monoclonal antibody allows highly targeted delivery of a therapeutic payload with minimal radiation delivered to normal tissues outside the tumor. The ability of nanoparticles to cross the blood brain barrier and reach the tumor cells themselves serves as proof of principle for potential potent therapeutic agents based on $^{225}$Ac nanoparticles.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

All ranges discussed can and do necessarily also describe all subranges therein for all purposes and that all such subranges are part this invention. Any listed range can be easily recognized as sufficiently describing and enabling the same range being broken down into at least equal halves (e.g., a lower half and upper half), thirds, quarters, tenths, etc.

What is claimed is:

1. An α-particle emitting nanoparticle comprising:

(a) an α-particle emitting core that comprises an α-emitting-radioisotope-doped $LnPO_4$; and (b) a sequestration shell enclosing the core that comprises $LnPO_4$ and is free of an α-emitting-radioisotope and that allows at least some of the α emissions from the α-emitting radioisotope to pass therethrough and reduces the release of radioactive decay products of the α-emitting radioisotope from the α-particle emitting nanoparticle compared to an otherwise equivalent α-particle emitting nanoparticle comprising the same α-particle emitting core but not comprising the sequestration shell enclosing the core; and wherein Ln of the α-particle emitting core and the sequestration shell are separately selectable lanthanide elements from the group consisting of La, Gd, Sm, Eu, Tb, Dy, Ho, Lu, Nd, Pm, and combinations thereof, and the α-particle emitting radioisotope is selected from the group consisting of $^{225}$AC, $^{223}$Ra, any radioactive decay products thereof, and combinations thereof, wherein the radioactive decay products of $^{225}$AC are selected from the group consisting of $^{221}$Fr, $^{217}$At, $^{213}$Bi, $^{213}$Po, $^{209}$Tl, $^{209}$Pb, and combinations thereof, and wherein the radioactive decay products of $^{223}$Ra are selected from the group consisting of $^{219}$Rn, $^{215}$Po, $_{211}$Pb, $^{211}$Bi, $_{207}$Tl, and combinations thereof.

2. The α-particle emitting nanoparticle of claim 1, wherein Ln comprises La.

3. The α-particle emitting nanoparticle of claim 2, wherein La is at least 25 mole percent of Ln.

4. The α-particle emitting nanoparticle of claim 2, wherein Ln further comprises Gd.

5. The α-particle emitting nanoparticle of claim 4, wherein La is at least 25 mole percent of Ln and Gd is at least 25 mole percent of Ln.

6. The α-particle emitting nanoparticle of claim 1, wherein the α-particle emitting radioisotope is at an amount that is greater than zero and up to about 2,000 ppm of the α-emitting-radioisotope-doped $LnPO_4$.

7. The α-particle emitting nanoparticle of claim 1, wherein the α-particle emitting radioisotope is at an amount that is greater than zero and up to about 200 ppm of the α-emitting-radioisotope-doped $LnPO_4$.

8. The α-particle emitting nanoparticle of claim 1, wherein the α-particle emitting radioisotope is selected from the group consisting of $^{225}$AC and the radioactive decay products thereof.

9. The α-particle emitting nanoparticle of claim 1, wherein the α-emitting-radioisotope-doped $LnPO_4$ is $\{La_{0.25\text{-}0.75}Gd_{0.25\text{-}0.75}\}(^{225}Ac)PO_4$.

10. The α-particle emitting nanoparticle of claim 1, wherein the α-emitting-radioisotope-doped $LnPO_4$ is $\{La_{0.40\text{-}0.60}Gd_{0.40\text{-}0.60}\}(^{225}Ac)PO_4$.

11. The α-particle emitting nanoparticle of claim 1, wherein the α-emitting-radioisotope-doped $LnPO_4$ is $\{La_{0.45\text{-}0.55}Gd_{0.45\text{-}0.55}\}(^{225}Ac)\}PO_4$.

12. The α-particle emitting nanoparticle of claim 1, wherein the α-emitting-radioisotope-doped $LnPO_4$ is $\{La_{0.50}Gd_{0.50}\}(^{225}Ac)PO_4$.

13. The α-particle emitting nanoparticle of claim 1, wherein the α-particle emitting core has a diameter that is in the range of about 1 nm to about 10 nm and the sequestration shell has a thickness that is in the range of about 1 nm to about 10 nm.

14. The α-particle emitting nanoparticle of claim 1, wherein the α-particle emitting core has a diameter that is in the range of about 2 nm to about 6 nm and the sequestration shell has a thickness that is in the range of about 1 nm to about 10 nm.

15. The α-particle emitting nanoparticle of claim 1, wherein the α-particle emitting core has a diameter that is about 4 nm and the sequestration shell has a thickness that is in the range of about 1 nm to about 5 nm.

16. The α-particle emitting nanoparticle of claim 1, wherein Ln of the sequestration shell is La.

17. The α-particle emitting nanoparticle of claim 1, wherein Ln of the sequestration shell is Gd.

18. The α-particle emitting nanoparticle of claim 1, wherein Ln of the sequestration shell is La and Gd.

19. The α-particle emitting nanoparticle of claim 1, wherein the sequestration shell comprises a multiplicity of layers, wherein Ln of each sequestration shell layer is separately selectable.

20. The α-particle emitting nanoparticle of claim 19, wherein each sequestration shell layer has a thickness that is in the range of about 0.2 nm to about 2 nm.

21. The α-particle emitting nanoparticle of claim 20, wherein the sequestration shell comprises a number of sequestration shell layers that is in the range of 2 to 5.

22. The α-particle emitting nanoparticle of claim 20, wherein the sequestration shell comprises 4 sequestration shell layers.

23. The α-particle emitting nanoparticle of claim 1, further comprising:

(c) an outer coating deposited on the sequestration shell, wherein the outer coating comprises gold.

24. The α-particle emitting nanoparticle of claim 23, wherein the outer coating has a thickness that is in the range of about 1 nm to about 60 nm.

25. The α-particle emitting nanoparticle of claim 23, wherein the outer coating has a thickness that is in the range of about 2 nm to about 25 nm.

26. The α-particle emitting nanoparticle of claim 23, wherein the outer coating further comprises one or more of the following gold isotopes $^{199}$Au, $^{198}$Au, and $^{197}$Au.

27. The α-particle emitting nanoparticle of claim 23, further comprising:

(d) a surface functionalization component adhered to the outer coating, wherein the surface functionalization component comprises a linker component and target component, and wherein the linker is selected from the group consisting of a lipoamide-PEG-acid, a lipoamide-PEG-amine, a lipoic acid-PEG-biotin, lipoic acid-PEG-N hydroxy succinimide, thio-PEG-N hydroxyl succinimide, thiol-PEG-Acid, thiol-PEG-amine, and combinations thereof, and the target component is selected from the group consisting of antibodies, aptamers, biotin, and peptides.

28. The α-particle emitting nanoparticle of claim 1, wherein a portion of the separately selectable Ln of the α-particle emitting core and the sequestration shell is a β-particle emitting radioisotope that is selected from the group consisting of $^{147}Nd$, $^{149}Pm$, $^{151}Pm$, $^{153}Sm$, $^{161}Tb$, $^{166}Ho$, $^{177}Lu$, and combinations thereof.

29. A method of making α-particle emitting nanoparticles, each comprising an α-particle emitting core, which comprises an α-emitting-radioisotope-doped $LnPO_4$, and a sequestration shell enclosing the core that allows at least some of the a emissions from the α-emitting radioisotope to pass therethrough and reduces the release of radioactive decay products of the α-emitting radioisotope from the α-particle emitting nanoparticle compared to otherwise equivalent α-particle emitting nanoparticle comprising the same α-particle emitting core but not comprising the sequestration shell enclosing the core, wherein the sequestration shell comprises one or more $LnPO_4$-containing layers and is free of an α-emitting-radioisotope, the method comprising:

(a) treating a colloidal suspension that comprises particles dispersed in a shell solution, wherein each particle comprises at least the α-particle emitting core, and wherein the shell solution comprises $Ln^{3+}$ cations and $PO_4$-containing anions, by controlling the pH, temperature, or both of the colloidal suspension to hydrolyze at least some of the $PO_4$-containing anions to form $(PO_4)^{3-}$ anions that react with $Ln^{3+}$ cations and form one $LnPO_4$-containing layer on the particles; and (b) repeating step (a) until the desired number of layers is deposited; and wherein Ln of the α-particle emitting core and each $LnPO_4$-containing layer are separately selectable lanthanide elements from the group consisting of La, Gd, Sm, Eu, Tb, Dy, Ho, Lu, Nd, Pm, and combinations thereof, wherein the α-particle emitting radioisotope is selected from the group consisting of $^{225}Ac$, $^{223}Ra$, any radioactive decay products thereof, and combinations thereof, wherein the radioactive decay products of $^{225}Ac$ are selected from the group consisting of $^{221}Fr$, $^{217}At$, $^{213}Bi$, $^{213}Po$, $^{209}Tl$, $^{209}Pb$, and combinations thereof, and wherein the radioactive decay products of $^{223}Ra$ are selected from the group consisting of $^{219}Rn$, $^{215}Po$, $^{211}Pb$, $^{211}Bi$, $^{207}Tl$, and combinations thereof.

30. The method of claim 29, wherein a source of the $PO_4$-containing anions is selected from the group consisting of monophosphates, diphosphates, polyphosphates, and combinations thereof.

31. The method of claim 29, wherein a source of the $PO_4$-containing anions is one or more tripolyphosphates.

32. The method of claim 29, wherein the sequestration shell comprises a number of $LnPO_4$-containing layers that is in the range of 1 to 5.

33. The method of claim 29, wherein the sequestration shell comprises 4 $LnPO_4$-containing layers.

34. The method of claim 29, wherein the particles are at an amount that is in the range of about 0.1 mg/mL to about 50 mg/mL of the colloidal suspension, the $Ln^{3+}$ cations are at an amount that is in the range of about 0.005 M to about 0.5 M in the shell solution, the $PO_4$-containing anions are tripolyphosphate ions that are at an amount that is in the range of about 0.01 M to about 1 M in the shell solution, and the ratio of $Ln^{3+}$ cations to tripolyphosphate ions is in the range of about 2:1 to about 1:4.

35. The method of claim 29, wherein the particles are at an amount that is in the range of about 1 mg/mL to about 30 mg/mL of the colloidal suspension, the $Ln^{3+}$ cations are at an amount that is in the range of about 0.01 M to about 0.1 M in the shell solution, the $PO_4$-containing anions are tripolyphosphate ions that are at an amount that is in the range of about 0.02 M to about 0.2 M in the shell solution, and the ratio of $Ln^{3+}$ cations to tripolyphosphate ions is in the range of about 1:1 to about 1:2.

36. The method of claim 29, wherein the treating of the colloidal suspension to form the $LnPO_4$-containing layer on the particles comprises controlling the temperature of the colloidal suspension such that it is in the range of about 60 to about 100° C. for a duration that is in the range of about 1 to about 5 hours.

37. The method of claim 29, wherein the treating of the colloidal suspension to form the $LnPO_4$-containing layer on the particles comprises controlling the temperature of the colloidal suspension such that it is in the range of about 85 to about 95° C. for a duration that is in the range of about 2 to about 4hours.

38. The method of claim 29, further comprising forming the α-particle emitting cores before forming $LnPO_4$-containing layer(s) of the sequestration shell, wherein the α-particle emitting cores are formed by treating a core solution, wherein the core solution comprises $Ln^{3+}$ anions, α-emitting-radioisotope ions, and $PO_4$-containing anions, by controlling the pH, temperature, or both of the core solution to hydrolyze at least some of the $PO_4$-containing anions to form $(PO_4)^{3-}$ anions thereby causing $Ln^{3+}$ cations and $(PO_4)^{3-}$ anions and α-emitting-radioisotope ions to form the α-particle emitting cores.

39. The method of claim 38, wherein the $Ln^{3+}$ ions are at an amount that is in the range of about 0.01 M to about 1 M in the core solution, $PO_4$-containing anions are tripolyphosphate ions that are at an amount that is in the range of about 0.02 M to about 2 M in the core solution, the ratio of $Ln^{3+}$ ions to tripolyphosphate ions is in the range of about 2:1 to about 1:4, and the α-emitting-radioisotope ions are at an amount that is up to about 100 mCi in the core solution.

40. The method of claim 38, wherein the $Ln^{3+}$ ions are at an amount that is in the range of about 0.02 M to about 0.2 M in the core solution, the $PO_4$-containing anions are tripolyphosphate ions that are at an amount that is in the range of about 0.04 M to about 0.4 M in the core solution, the ratio of $Ln^{3+}$ ions to tripolyphosphate ions is in the range of about 1:1 to about 1:2, and the α-emitting-radioisotope ions are at an amount that is up to about 10 mCi of the core solution.

41. The method of claim 29, further comprising depositing on the sequestration shells of the particles an outer coating that comprises gold by obtaining a mixture comprising the particles, solute gold ions, and solute citrate ions, and reducing the solute gold ions such that at least some of the gold comes out of solution and deposits on the sequestration shells thereby forming the outer coating.

42. The method of claim 41, wherein the mixture is formed by mixing a particle solution comprising the particles and the citrate ions and a gold-containing solution, and wherein the gold is at an amount that is in the range of about 0.1 mM to about 10 mM in the gold-containing solution, the citrate is at an amount that is in the range of about 0.001 M to about 0.1 M of the particle solution, the particles are at an amount that is in the range of about 0.1 mg/mL to about 10 mg/mL of the mixture, and the mass ratio of solute gold to particles to citrate in the mixture is about 0.6-60:0.1-10:1.2-120.

43. The method of claim 41, wherein the mixture is formed by mixing a particle solution comprising the particles and the citrate ions and a gold-containing solution, and wherein the gold is at an amount that is in the range of about 0.5 mM to about 5 mM in the gold-containing solution, the citrate is at an amount that is in the range of about 0.005 M to about 0.05 M in the particle solution, the particles are at an amount that is in the range of about 0.5 mg/mL to about 5 mg/mL in the mixture, and the mass ratio of solute gold to particles to citrate in the mixture is about 3-9:0.5-2:6-18.

44. The method of claim 41, wherein reducing the gold ions comprises controlling the temperature of the mixture such that it is in the range of about 50 to about 100° C. for a duration that is in the range of about 0.3 to about 3 hours.

45. The method of claim 41, wherein reducing the gold ions comprises controlling the temperature of the mixture such that it is in the range of about 70 to about 95° C. for a duration that is in the range of about 0.5 to about 1.5 hours.

46. The method of claim 30, further comprising adhering a surface functionalization component to the outer coating, wherein the surface functionalization component comprises a linker component and target component, and wherein the linker is selected from the group consisting of a lipoamide-PEG-acid, a lipoamide-PEG-amine, a lipoic acid-PEG-biotin, lipoic acid-PEG-N hydroxy succinimide, thio-PEG-N hydroxyl succinimide, thiol-PEG-Acid, thiol-PEG-amine, and combinations thereof, and the target component is selected from the group consisting of antibodies, aptamers, biotin, and peptides.

47. A method of depositing a coating comprising gold on α-particle emitting nanoparticles having $LnPO_4$ surfaces, the method comprising treating a mixture comprising the nanoparticles, solute gold ions, and solute citrate ions to reduce solute gold ions so that at least some of the gold comes out of solution and deposits on the surfaces of the nanoparticles thereby forming the coatings, wherein the mixture is formed by mixing a particle solution and a gold-containing solution, wherein the particle solution comprises the nanoparticles and the citrate ions, wherein the gold-containing solution contains an amount of gold that is in the range of about 0.1 mM to about 10 mM, wherein the citrate is at an amount that is in the range of about 0.001 M to about 0.1 M of the particle solution, wherein the nanoparticles are at an amount that is in the range of about 0.1 mg/mL to about 10 mg/mL of the mixture, wherein the mass ratio of solute gold to nanoparticles to citrate in the mixture is about 0.6-60:0.1-10:1.2-120, and wherein the treating comprises controlling the temperature of the mixture such that it is in the range of about 50 to about 100° C. for a duration that is in the range of about 0.3 to about 3 hours.

48. The method of claim 47, wherein the gold is at an amount in the range of about 0.5 mM to about 5 mM in the gold-containing solution, the citrate is at an amount that is in the range of about 0.005 M to about 0.05 M of the particle solution, the nanoparticles are at an amount that is in the range of about 0.5 mg/mL to about 5 mg/mL in the mixture, and the mass ratio of solute gold to nanoparticles to citrate is 3-9:0.5-2:6-18, and wherein the treating comprises controlling the temperature of the mixture such that it is in the range of about 70 to about 95° C. for a duration that is in the range of about 0.5 to about 1.5 hours.

49. A composition for targeted in vivo generated alpha radiotherapy, the composition comprising:

(a) phosphate buffered saline; and (b) a multiplicity of α-particle emitting nanoparticles, wherein each such α-particle emitting nanoparticle comprises:

(i) an α-particle emitting core that comprises an α-emitting-radioisotope-doped $LnPO_4$; and (ii) a sequestration shell enclosing the core that comprises $LnPO_4$ and that is essentially free of the α-emitting-radioisotope, wherein the sequestration shell allows at least some of the α emissions from the α-emitting radioisotope to pass therethrough and reduces the release of radioactive decay products of the α-emitting radioisotope from the α-particle emitting nanoparticle compared to an otherwise equivalent α-particle emitting nanoparticle comprising the same α-particle emitting core but not comprising the sequestration shell enclosing the core; and (iii) an outer coating deposited on the sequestration shell that comprises gold; and (iv) a surface functionalization component adhered to the outer coating, wherein the surface functionalization component comprises a linker component and target component, and wherein the linker is selected from the group consisting of a lipoamide-PEG-acid, a lipoamide-PEG-amine, a lipoic acid-PEG-biotin, lipoic acid-PEG-N hydroxy succinimide, thio-PEG-N hydroxyl succinimide, thiol-PEG-Acid, thiol-PEG-amine, and combinations thereof, and the target component is selected from the group consisting of antibodies, aptamers, biotin, and peptides; and wherein Ln of the α-particle emitting core and the sequestration shell are separately selectable lanthanide elements from the group consisting of La, Gd, Sm, Eu, Tb, Dy, Ho, Lu, Nd, Pm, and combinations thereof, and the α-particle emitting radioisotope is selected from the group consisting of $^{225}$AC, $^{223}$Ra, any radioactive decay products thereof, and combinations thereof, wherein the radioactive decay products of $^{225}$AC are selected from the group consisting of $^{221}$Fr, $^{217}$At, $^{213}$Bi, $^{213}$Po, $^{209}$Tl, $^{209}$Pb, and combinations thereof, and wherein the radioactive decay products of $^{223}$Ra are selected from the group consisting of $^{219}$Rn, $^{215}$Po, $^{211}$Pb, $^{211}$Bi, $^{207}$Tl, and combinations thereof.

50. A method for conducting targeted in vivo generated alpha radiotherapy, the method comprising administering to a patient an effective amount of a composition comprising:

(a) phosphate buffered saline; and (b) a multiplicity of α-particle emitting nanoparticles, wherein each such α-particle emitting nanoparticle comprises:

(i) an α-particle emitting core that comprises an α-emitting-radioisotope-doped $LnPO_4$; and (ii) a sequestration shell enclosing the core that comprises $LnPO_4$ and that is essentially free of the α-emitting-radioisotope, wherein the sequestration shell allows at least some of the α emissions from the α-emitting radioisotope to pass therethrough and reduces the release of radioactive decay products of the α-emitting radioisotope from the α-particle emitting nanoparticle compared to an otherwise equivalent α-particle emitting nanoparticle comprising the same α-particle emitting core but not comprising the sequestration shell enclosing the core; and (iii) an outer coating deposited on the sequestration shell that comprises gold; and (iv) a surface functionalization component adhered to the outer coating, wherein the surface functionalization component comprises a linker component and target component, and wherein the linker is selected from the group consisting of a lipoamide-PEG-acid, a lipoamide-PEG-amine, a lipoic acid-PEG-biotin, lipoic acid-PEG-N hydroxy succinimide, thio-PEG-N hydroxyl succinimide, thiol-PEG-Acid, thiol-PEG-amine, and combinations thereof, and the target component is selected from the group consisting of antibodies, aptamers, biotin, and peptides; and wherein Ln of the α-particle emitting core and the sequestration shell are separately selectable lanthanide elements from the group consisting of La, Gd, Sm, Eu, Tb, Dy, Ho, Lu, Nd, Pm, and combinations thereof, and the α-particle emitting radioisotope is selected from the group consisting of $^{225}$AC, $^{223}$Ra, any radioactive decay products thereof, and combinations thereof, wherein the radioactive decay products of $^{225}$AC are selected from the group consisting of $^{221}$Fr, $^{217}$At, $^{213}$Bi, $^{213}$Po, $^{209}$Tl, $^{209}$Pb, and combinations thereof, and wherein the radioactive decay products of $^{223}$Ra are selected from the group consisting of $^{219}$Rn, $^{215}$Po, $^{211}$Pb, $^{211}$Bi, $^{207}$TI, and combinations thereof.

51. The method of claim 50, wherein the α-particle emitting core comprises Gd, the sequestration shell comprises Gd, or both the α-particle emitting core and the sequestration shell comprise Gd, and wherein the method further comprises determining the locations of the α-particle emitting nanoparticles in the patient by conducting magnetic resonance imaging of the patient after administration of the composition.

52. The method of claim 50, wherein the outer coating comprises $^{199}$Au, and wherein the method further comprises determining the locations of the α-particle emitting nanoparticles in the patient by conducting single-photon emission computed tomography imaging of the patient after administration of the composition.

53. A β-particle emitting nanoparticle comprising an β-particle emitting core that comprises an β-emitting-radioisotope-doped $LnPO_4$, an outer coating deposited on the core that comprises gold, and a surface functionalization component adhered to the outer coating, wherein Ln are lanthanide elements from the group consisting of La, Gd, Sm, Eu, Tb, Dy, Ho, Lu, Nd, Pm, and combinations thereof, and wherein some portion of the Ln is a β-particle emitting radioisotope that is selected from the group consisting of $^{147}$Nd, $^{149}$Pm, $^{151}$Pm, $^{153}$Sm, $^{161}$Tb, $^{166}$Ho, $^{177}$Lu, and combinations, wherein the surface functionalization component comprises a linker component and target component, and wherein the linker is selected from the group consisting of a lipoamide-PEG-acid, a lipoamide-PEG-amine, a lipoic acid-PEG-biotin, lipoic acid-PEG-N hydroxy succinimide, thio-PEG-N hydroxyl succinimide, thiol-PEG-Acid, thiol-PEG-amine, and combinations thereof, and the target component is selected from the group consisting of antibodies, aptamers, biotin, and peptides.

* * * * *